United States Patent [19]
Rowan

[11] 3,945,938
[45] Mar. 23, 1976

[54] ANTIBACTERIAL DITHIOCARBAMATE ESTER DETERGENT COMPOSITIONS

[75] Inventor: Eugene VanNess Rowan, Rowayton, Conn.

[73] Assignee: R. T. Vanderbilt Company, Inc., East Norwalk, Conn.

[22] Filed: May 7, 1974

[21] Appl. No.: 467,714

[52] U.S. Cl. ............ 252/107; 252/106; 260/455 A; 424/300
[51] Int. Cl.² ........................ C11D 3/48; C11D 9/50
[58] Field of Search ........ 252/106, 107; 260/455 A; 424/300

[56] References Cited
UNITED STATES PATENTS

| | | | |
|---|---|---|---|
| 2,474,839 | 7/1949 | Gresham et al. | 260/429 |
| 2,692,862 | 10/1954 | Lipsitz | 252/107 |
| 2,786,866 | 3/1957 | Hook et al. | 260/455 |
| 3,156,717 | 11/1964 | Rossi | 260/455 |
| 3,398,181 | 8/1968 | Karsten et al. | 260/455 |
| 3,506,578 | 4/1970 | Karsten et al. | 252/107 |

FOREIGN PATENTS OR APPLICATIONS

| 824,196 | 11/1959 | United Kingdom |
|---|---|---|

Primary Examiner—P. E. Willis, Jr.
Attorney, Agent, or Firm—Roland T. Bryan

[57] ABSTRACT

Antibacterial and germicidal detergent compositions containing biologically active S-(1,2-dialkoxycarbonylethyl)dialkyldithiocarbamates of the formula:

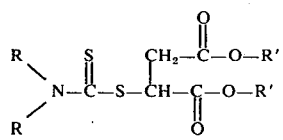

where R and R' represent lower alkyl groups. The compositions unexpectedly posssess effective skin substantivity so that soap and shampoo formulations, as well as cosmetic and toilet preparations retaining bacteriostatic and germicidal activity even after washing and rinsing of the skin are obtained.

5 Claims, No Drawings

ANTIBACTERIAL DITHIOCARBAMATE ESTER DETERGENT COMPOSITIONS

BACKGROUND OF THE INVENTION

1. Field of the Invention

The present invention relates to the use of certain S-(1,2-dialkoxycarbonylethyl) dialkyldithiocarbamates as bacteriostats and germicides and more particularly to their use as active ingredients in detergent compositions used for skin cleansing. The bacteriostatic detergent compositions find advantageous applicability in medicinal and germicidal bar and liquid soaps and shampoos as well as in other cosmetic and toilet preparations including cosmetic cleansing creams, shaving creams, hair treatment preparations and the like.

While numerous substances posses a degree of bacteriostatic effectiveness against specific bacteria or groups thereof, few produce the desired results necessary for a successful soap bacteriostat. In many cases, the bacteriostatic activity of known bactericides is reduced or inactivated in the presence of surface active agents such as soaps or detergents. Furthermore, even if its activity is not reduced in soap, a bactericide may nevertheless be ineffective in inhibiting skin microorganisms for any length of time due to a lack of effective skin substantivity, i.e., the property of remaining on the skin and retaining antibacterial and germicidal activity over a period of time after washing and rinsing of the skin. Besides antibacterial properties, other desirable properties are important for commercial application of a soap bacteriostat. After incorporation of the soap bacteriostat, the detergent composition such as bar, powder, paste, liquid, or aerosol must maintain the desired antimicrobial efficacy as well as retain the following properties: initial whiteness, odor stability color stability under aging and sunlight exposure, and absence of discoloration in the presence of copper.

2. Description of the Prior Art

S-(1,2-dialkoxycarbonylethyl) dialkyldithiocarbamates are known to possess fungicidal and herbicidal properties. See for example, U.S. Pat. No. 2,786,866. British Pat. No. 824,196 discloses certain S-ethoxycarbonyl esters of N,N-dialkyldithiocarbamates which retain their bacteriostatic activity in the presence of soaps and waxes. That patent further states that the retention of such activity appears to be a property highly specific to compounds of the particular structure concerned since modification of the structure generally results in loss thereof. Moreover, the references give no indication that the bactericides possess skin substantivity, an important criteria for use as active ingredients in bacteriostatic toilet and cosmetic formulations.

Therefore, the prior art compounds may be considered as specific and unsuggestive of other compounds of the class possessing properties necessary for an effective skin substantive soap bacteriostat.

SUMMARY OF THE INVENTION

It has been discovered according to this invention that certain S-(1,2-dialkoxycarbonylethyl) dialkyldithiocarbamate compounds possess specific antibacterial properties that are advantageously retained in the presence of detergents for prolonged periods of time and unexpectedly exhibit effective skin substantivity. Furthermore, those compounds meet other criteria desirable for an effective soap bacteriostat. For example, detergent compositions containing the compounds of the invention possess initial whiteness, stability of color and long shelf life with respect to the active ingredient.

The aforementioned advantages are obtained according to this invention by providing antibacterial and germicidal detergent compositions containing as active ingredients S-(1,2-dialkoxycarbonylethyl) dialkyldithiocarbamates of the general formula:

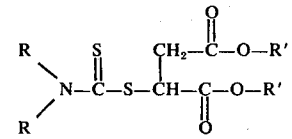

where R and R' represent, independent of each other, methyl and ethyl groups, provided that the total number of carbon atoms in the four alkyl groups is six or less.

Therefore, it is an object of this invention to provide microorganism inhibiting methods and detergent compositions displaying antibacterial and germicidal activity on the skin for a period of time after washing and rinsing of the skin.

The term "detergent" as used herein is intended to include natural and synthetic organic detergents such as soap as well as non-soap surface-active agents of the anionic, cationic, nonionic and amphoteric type. Furthermore, the term detergent is intended to cover all products in which soap and non-soap surface-active agents are major constituents, for example bar soap, liquid soaps, shaving creams, cosmetic cleansing creams, hair and scalp treatment preparations such as shampoos and similar formulations.

A further object of this invention is the provision of shampoo or detergent compositions containing S-(1,2-dialkoxycarbonylethyl) dialkyldithiocarbamate compounds of the invention that are substantive to the skin and that give prolonged effect in reducing the number of microorganisms on skin.

Other objects and advantages will become apparent from the detailed description which follows.

DESCRIPTION OF THE PREFERRED EMBODIMENTS

The compounds of this invention are prepared by general, known methods. For example, U.S. Pat. No. 2,786,866 describes the addition of a dithiocarbamic acid formed in situ to a compound having an activated carbon to carbon double bond to yield esters of dithiocarbamic acid. To further illustrate, S-(1,2-dimethoxycarbonylethyl) dimethyldithiocarbamte is prepared as follows:

A mixture of 100 g. methanol and 38 g. carbon disulfide is placed in a reaction vessel equipped with condenser and stirrer and cooled in an ice bath to 35°C. While maintaining this temperature, 22.5 g. anhydrous dimethylamine is slowly added to the mixture, followed by the addition of 72 g. dimethyl maleate. The reaction mixture is heated to 45°–50°C and allowed to react for 1½ hours. Methanol is stripped off under vacuum to yield 129.5 g. (99.5% of theory) of yellow, oil-insoluble liquid.

Relatively small amounts of the antibacterial agents in detergent compositions are sufficient to obtain the advantages of the invention. Satisfactory results are obtained when the weight of the antibacterial agent is from 0.1 to 5% based on the weight of the detergent composition, with the desired range being 1 to 3%. Greater amounts will be effective but further substantial advantages will be minimal or nonexistant. The effective amounts will vary for a given application and/or desired germicidal or biostatic effect and may be determined by those skilled in the art according to known practice.

The germicidal agents of this invention can be added to soap or other skin cleansing agent by any of the commonly employed methods which result in a uniform distribution of the anitbacterial agent throughout the entire mass. Shampoo and soap formulations can, of course, contain any of the usual additives such as coloring agents, perfume, thickeners, solvents, opacificers, suds builders, conditioning agents, preservatives, buffers, antioxidants and anti-static agents. The germicidal agents of the invention can be employed in conjunction with other bacteriostats, as for instances, phenols, carbanilides, salicylanilides or any other suitable bacteriostat or bactericide. The detergents may be soap as well as non-soap surface active agents of the anionic, cationic, nonionic and amphoteric type.

Anionic detergents include both the soap and non-soap detergents. Examples of suitable soaps are the sodium, potassium, ammonium and alkanolammonium salts of higher fatty acids ($C_{10}$–$C_{20}$). Particularly useful are the sodium and potassium salts of the mixtures of fatty acids derived from coconut oil and tallow. Examples of anionic non-soap detergents are alkyl glyceryl ether sulfonates, alkyl sulfates, alkyl monoglyceride sulfates or sulfonates, alkyl polyethoxy ether sulfates, acyl sarcosinates, acyl esters of isethionates, acyl N-methyl taurides, alkyl benzene sulfonates, and alkyl phenol polyethoxy sulfonates. In these compounds the alkyl and acyl groups, respectively, contain 10 to 20 carbon atoms. They are used in the form of water-soluble salts, the sodium, potassium, ammonium and alkanolammonium salts, for example. Specific examples are sodium lauryl sulfate, potassium N-methyl lauroyl tauride; and triethanolamine dodecyl benzene sulfonate.

Suitably useful cationic detergents are quaternary ammonium salts as exemplified by dilauryldimethyl ammonium chloride, cetyl trimethyl ammonium bromide, N-cetylpyridinium bromide and benzethonium chloride.

Nonionic detergents include ethoxylated alkylphenols, ethoxylated aliphatic alcohols, carboxylic esters and carboxylic amides. Particularly useful are polyoxyethylene alkylphenols, polyoxyethylene fatty ethers, polyoxyethylene fatty acid esters and ethoxylated alkylolamides.

Representative examples of amphoteric detergents are alkyl beta-imino-dipropionates, and alkyl beta-amino-propionates, wherein the alkyl group contains 10 to 20 carbon atoms, and basic quaternary ammonium compounds derived from 2-alkyl-substituted imidazoline.

The specific procedures used to test the properties hereinbefore enumerated are described in the following examples with the results obtained set forth in the tables.

EXAMPLE 1 a. Soap Plug Test

Bacteriostatic activity per se was tested by milling into Ivory soap (made according to U.S. Pat. No. 2,295,594) 1% of the test material based on the weight of the soap and by compressing it into plugs. Plugs (0.5 inch in diameter and 0.25 inch thick) of each of the test soaps were placed on agar plates seeded with one of three representative test bacteria, *Bacillus subtilis*, *Staphylococcus aureus*, and *Salmonella typhosa*. After incubation at 37°C. for 24 hrs., the clear zone of inhibition (lack of bacterial growth) was measured and reported as average diameter of zone inhibition (diameter of clear zone less the diameter of the soap plug), and tabulated in Table IA.

b. Hide Substantivity (soap)

For the test of substantivity or retention of bacteriostat by the skin after washing with the test soap, untanned calf-skin hide buttons were soaked in 100 ml. of 8% solution of the test soap containing 1% of the test material, rinsed four times with 100 ml. distilled water, placed on seeded agar plates and incubated for 24 hrs., at optimum temperature of the test bacteria, *Bacillus subtilis*, *Staphylococcus aureus* and *Salmonella typhosa*. The zones of inhibition were measured and reported as in the soap plug test, and tabulated in Table IA.

The test soap containing the active ingredient was aged for several months and the test was repeated.

TABLE IA

| | | BACTERIOSTATIC ACTIVITY AND SUBSTANTIVITY IN SOAP | | | | | |
|---|---|---|---|---|---|---|---|
| | | Average Diameter of Inhibited Zone In mm | | | | | |
| Active Ingredient | Aging Time | A) Activity In Soap | | | B) Hide Substantivity In Soap | | |
| | | B. subtilis | S. aureus | S. typhosa | B. subtilis | S. aureus | S. typhosa |
| S-(1,2-dimethoxycarbonyl-ethyl) dimethyldithiocarbamate | 24 hours | 24 | 32 | 23 | 8 | 11 | 6 |
| | 1 month | — | — | — | 8 | 10 | 11 |
| | 4 months | — | — | — | 9 | 12 | 7 |
| S-(1,2-diethoxycarbonyl-ethyl) dimethyldithiocarbamate | 24 hours | 18 | 27 | 22 | 4 | 2 | 1 |
| | 2 months | — | — | — | 5 | 17 | 7 |
| S-(1,2-dimethoxycarbonyl-ethyl) diethyldithiocarbamate | 24 hours | 10 | 16 | 12 | 3 | 4 | 2 |
| | 2 months | — | — | — | 6 | 6 | 2 |

The results compiled in Table IA demonstrate the good microorganism inhibiting and skin substantive properties possessed by the compounds of this invention. As indicated by the aging tests, these desirable properties are retained in soap media over prolonged periods of time. The unexpected effectiveness of the S-(1,2-dialkoxycarbonylethyl) dialkyldithiocarbamates in the presence of detergents according to the invention is more evident in comparison with the virtual inactivity and ineffectiveness of the higher alkyl derivatives of the dithiocarbamate esters of the invention. The results tabulated in Table IB demonstrate a lack of substantial bacteriostatic activity and skin substantivity in soap for these analogous compounds and thus, the unexpected efficacy of the compounds in the compositions of the invention.

TABLE IB

HIGHER ALKYL DERIVATIVE DITHIOCARBAMATES WITHOUT SUBSTANTIAL BACTERIOSTATIC ACTIVITY AND SUBSTANTIVITY IN SOAP

| Active Ingredient | Average Diameter of Inhibited Zone in mm | | | | | |
|---|---|---|---|---|---|---|
| | A) Activity In Soap | | | B) Hide Substantivity In Soap | | |
| | B. subtilis | S. aureus | S. typhosa | B. subtilis | S. aureus | S. typhosa |
| S-(1,2-dimethoxycarbonylethyl) di-n-propyldithiocarbamate | 0 | 0 | 0 | 0 | 0 | 0 |
| S-(1,2-diethylcarbonylethyl) dibutyldithiocarbamate | 0 | 0 | 0 | 0 | 0 | 0 |
| S-(1,2-dioctylcarbonylethyl) diethyldithiocarbamate | 0 | 4 | 0 | 0 | 0 | 0 |

EXAMPLE II

The skin substantivity test was repeated by using a shampoo formulation as follows:

| Ingredients | Percent By Weight |
|---|---|
| Sodium salt of sulfated coconut fatty alcohol | 23.0 |
| Sodium stearate | 8.7 |
| Sodium sulfate | 0.8 |
| Trisodium phosphate | 2.1 |
| Perfume | 1.0 |
| Active Ingredient: S-(1,2-dimethoxycarbonylethyl) dimethyldithiocarbamate | 2.0 |
| Water, made up to 100% | — |
| pH | 7.7 |

Untanned calf-skin buttons were soaked in 100 ml. of 8% solution of the test shampoo containing 2% of the test material, rinsed four times with 100 ml of distilled water, placed on seeded agar plates and incubated for 24 hrs. at optimum growth temperature of the test bacteria, *Bacillus subtilis*, *Staphylococcus aureus* and *Salmonella typhosa*. The zones of inhibition were measured and reported as in the soap plug test and tabulated in Table II.

TABLE II

| | Hide Substantivity in Shampoo Average Diameter of Inhibited Zone in mm | | |
|---|---|---|---|
| Active Ingredient | B. subtilis | S. aureus | S. typhosa |
| S-(1,2-dimethoxycarbonylethyl) dimethyldithiocarbamate | 10 | 18 | 8 |
| S-(1,2-diethoxycarbonylethyl) dimethyldithiocarbamate | 12 | 10 | 7 |
| S-(1,2-dimethoxycarbonylethyl) diethyldithiocarbamate | 2 | 2 | 1 |

The test results demonstrate the bacteriostatic activity and skin substantive properties of the compound of this invention in a shampoo media.

EXAMPLE III

To test the color stability of detergent compositions, a soap plug containing S-(1,2-dimethoxycarbonylethyl) dimethyldithiocarbamate as active ingredient was cut in two, and one portion was exposed to sunlight for 40 hrs. Upon comparison to the unexposed portion of the soap, no color change was observed.

Thus, there have been disclosed S-(1,2-dialkoxycarbonylethyl) dialkyldithiocarbamates which unexpectedly possess excellent germicidal and skin substantive properties which are retained in the presence of detergents after storage. These properties, as well as the color stability of the compounds indicate their applicability as active ingredients in germicidal or medicinal soaps, shampoos and other skin-cleansing and cosmetic compositions.

I claim:

1. A bacteriostatic skin and scalp cleansing composition comprising detergent and a biostatically effective amount of a skin substantive compound of the general formula:

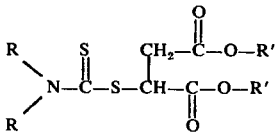

where R and R' represent, independent of each other, methyl and ethyl groups provided that the total number of carbon atoms in the four alkyl groups is six or less.

2. A bacteriostatic skin and scalp cleansing composition as claimed in claim 1 where the biostatically effective amount is 0.1 to 5 percent by weight based on the total weight of the composition.

3. A bacteriostatic skin and scalp cleansing composition as claimed in claim 1 where the detergent is shampoo.

4. A biostatically active detergent composition comprising at least one synthetic organic detergent selected from the group consisting of anionic, nonionic, cationic and amphoteric detergents and fatty acid soaps and a biostatically effective amount of a skin substantive, biologically active agent selected from the group consisting of S-(1,2-dimethoxycarbonylethyl) dimethyldithiocarbamate, S-(1,2-diethoxycarbonylethyl) dimethyldithiocarbamate, S-(1,2-dimethoxycarbonylethyl) diethyldithiocarbamate, and combinations thereof.

5. A method of inhibiting the growth of skin microorganisms by applying thereto a cleansing composition including at least one synthetic organic detergent selected from the group consisting of anionic, nonionic, cationic, and amphoteric detergents and fatty acid soaps and from 0.1 to 5 percent by weight based on the total weight of the composition of a compound of the general formula:

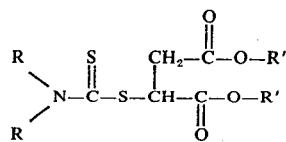

where R and R' represent independent of each other methyl and ethyl groups provided that the total number of carbon atoms in the four alkyl groups is six or less.

* * * * *